(12) United States Patent
Besson

(10) Patent No.: US 6,341,154 B1
(45) Date of Patent: Jan. 22, 2002

(54) METHODS AND APPARATUS FOR FAST CT IMAGING HELICAL WEIGHTING

(75) Inventor: Guy M. Besson, Wauwatosa, WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 09/602,153

(22) Filed: Jun. 22, 2000

(51) Int. Cl.$^7$ ................................................. A61B 6/03
(52) U.S. Cl. ........................................... 378/15; 378/901
(58) Field of Search ............................. 378/4, 15, 901

(56) References Cited

U.S. PATENT DOCUMENTS

| | | | | |
|---|---|---|---|---|
| 5,606,585 A | * | 2/1997 | Hu | 378/15 |
| 5,974,110 A | * | 10/1999 | Hu | 378/15 |

OTHER PUBLICATIONS

D.L. Parker, "Optimization Of Short Scan Convolution Reconstruction In Fan Beam CT," IEEE, 1982, pp. 199–202.
G. Besson, "New Classes Of Helical Weighting Algorithms With Applications To Fast CT Reconstruction," Med. Phys. 25 (8), Aug. 1998, pp. 1521–1532.
H. Hu and Y. Shen, "Helical CT Reconstruction With Longitudinal Filtration," Med. Phys. 25(11), Nov. 1998, pp. 2130–2138.
H. Hu, "Multi–slice Helical CT: Scan And Reconstruction," Med. Phys. 26(1), Jan. 1999, pp. 5–18.
J. Hsieh, "An Optimized Reconstruction Algorithm For Temporal Resolution Improvement In C^T Fluoroscopy" Radiology 209 (p), pp. 435, 1998.

* cited by examiner

*Primary Examiner*—David V. Bruce
(74) *Attorney, Agent, or Firm*—Armstrong Teasdale LLP; Christian G. Cabou

(57) ABSTRACT

In one embodiment, the present invention is a method for reconstructing a computed tomographic image of an object that includes steps of: helically scanning an object with a multislice CT imaging system to collect projection data; identifying a center view of the collected projection data; performing an operation selected from the group of helical interpolation and helical extrapolation on the collected projection data to produce super-views of the object; weighting an angular range of the super-views with normalized helical weights, the normalized helical weights being dependent upon whether interpolation or extrapolation was performed; and backprojecting the weighted super-views to produce a reconstricted image of the object.

22 Claims, 1 Drawing Sheet

US 6,341,154 B1

METHODS AND APPARATUS FOR FAST CT IMAGING HELICAL WEIGHTING

BACKGROUND OF THE INVENTION

This invention relates generally to methods for computed tomographic (CT) imaging, and more specifically to methods and apparatus for rapidly reconstructing helically scanned images.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array f radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. In a helical scan, a table supporting the object moves through the gantry as it scans.

In a multislice imaging system, the detector comprises a plurality of parallel detector rows. A multislice detector is capable of providing a plurality of images representative of a volume of an object. Each image of the plurality of images corresponds to a separate "slice" of the volume. The thickness or aperture of the slice is dependent upon the thickness of the detector rows. It is also known to selectively combine data from a plurality of adjacent detector rows (i.e., a "macro row") to obtain images representative of slices of different selected thicknesses.

One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display. Imaging programs of one known CT imaging system rely on a 2-dimensional (2D) backprojection. Accordingly, cone angles of the individual line integrals are ignored and all the rays acquired at a given source position and at a given detector row are described as belonging to a single plane orthogonal to the z axis. This plane is uniquely described by its z-distance to the gantry plane. The "gantry plane" is a plane orthogonal to a z-axis (or patient axis) and passing through the center of the focal spot. In general, the gantry plane exactly bisects the detector in z, that is, it passes between two rows of the detector. Due to the fact that a 2D backprojection is used for reconstruction, all fan rays measured by a detector macro-row (for a given source position) are assumed to be coplanar, in a plane orthogonal to z. The associated plane of reconstruction (POR) is uniquely characterized by its distance to the gantry plane, which distance depends upon a selected imaging aperture. The POR intersects the z-axis where the center (in z) of the associated macro-row projects.

In a "high speed" (HS) mode of a CT imaging system, the width of the detector crosses a POR of an image in a fraction of a full rotation. Specifically, in one known CT imagining system, this fraction is $4/6$ (=0.67) for a four-slice scanner at 6:1 pitch, from detector edge to detector edge (allowing for some data extrapolation, over half a macro-row); $3/6$ (=0.5) for a four slice scanner at 6:1 pitch, without data extrapolation; $8/11$ (=0.73) for an eight slice scanner at 11:1 pitch, from detector edge to detector edge; and $7/11$ (=0.64) for an eight slice scanner at 11:1 pitch, without data extrapolation. These fractions are to be compared with the fraction necessary for half-scan reconstruction, which is $(\pi+2\Gamma)/(2\pi)$= 0.65, where $\Gamma$ is the maximum fan angle.

Therefore, it is seen that known HS modes barely provide enough data for half-scan reconstruction (that is, they provide just enough data when allowing for a small amount of extrapolation from the detector rows). It is also seen that at a pitch of 11:1 for one known eight slice system, just enough data is provided for image reconstruction from a half-scan data acquisition.

Known helical weighting algorithms require a large number of super-views, i.e., sets of projection data acquired at a given view angle, with as many projections as detector rows. Based on the considerations above, it would be desirable to provide methods and apparatus for reconstruction of images that require a reduced number of super-views and reduced processing time. It would further be desirable to provide methods and apparatus for reconstruction of images that provide improved temporal resolution.

BRIEF SUMMARY OF THE INVENTION

In one embodiment, the present invention is a method for reconstructing a computed tomographic image of an object that includes steps of: helically scanning an object with a multislice CT imaging system to collect projection data; identifying a center view of the collected projection data; performing an operation selected from the group of helical interpolation and helical extrapolation on the collected projection data to produce super-views of the object; weighting an angular range of the super-views with normalized helical weights, the normalized helical weights being dependent upon whether interpolation or extrapolation was performed; and backprojecting the weighted super-views to produce a reconstructed image of the object.

This embodiment provides an advantage of requiring a reduced number of super-views and reduced processing time compared to known image reconstruction methods. In addition, improved temporal resolution relative to known methods is also provided.

DETAILED DESCRIPTION OF THE INVENTION

Figure 1:
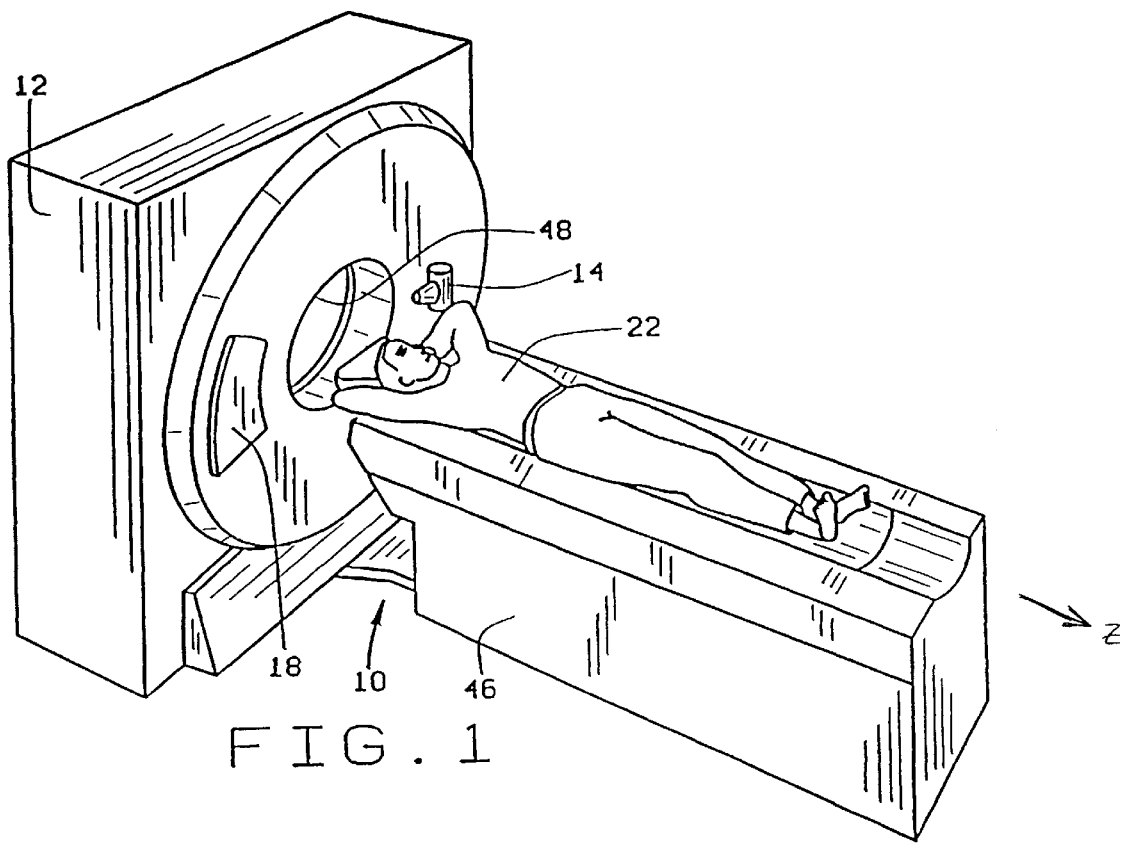
FIG. 1 is a pictorial view of a CT imaging system.
Figure 2:
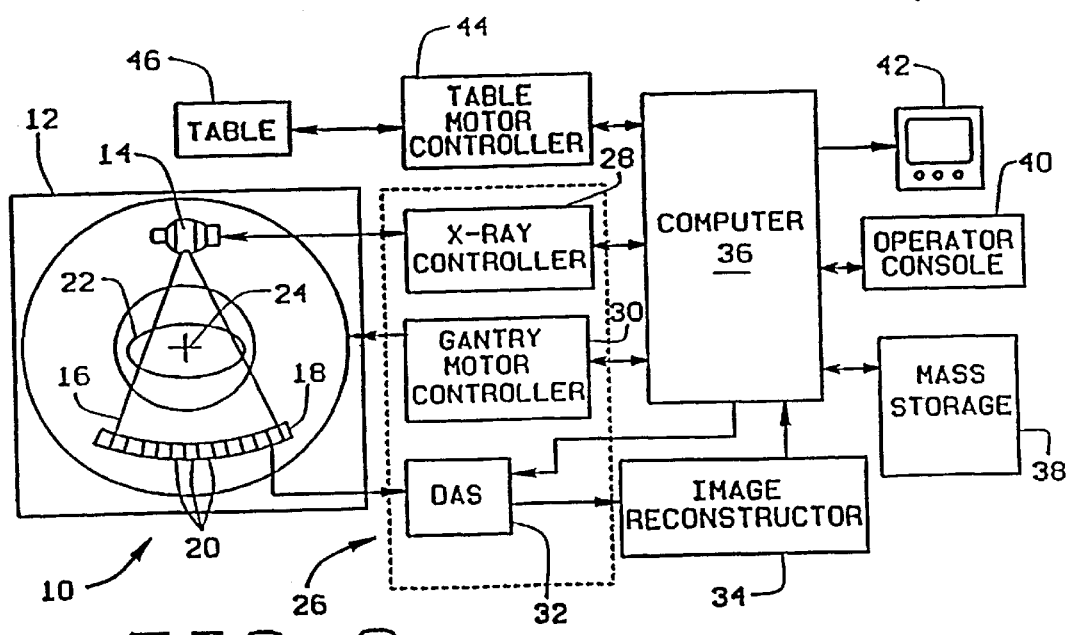
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Detector array 18 is fabricated in a multislice configuration having multiple parallel rows of detector elements 20. (Only one row of detector elements 20 is shown in the Figures.) Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstricted image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment of the present invention, the following steps are performed for reconstruction of a specific image plane of an object 22 such as a patient. First, an operating mode of a multislice CT imaging system is selected. For example, a high speed (HS), high-quality (HQ), or fast high quality (HQ-F) mode is selected. The object is then helically scanned with the multislice CT imaging system in accordance with the selected operating mode to collect projection data. From the collected projection data, a center view is identified for an image plane to be reconstructed. The identified center view is then used to select an angular range of super-views of the collected projection data that contribute to a reconstruction of an image of a desired region of the object. The "center view" of the collected projection data is a view that is within the POR or is closest in z to the POR center. The center view enables identification of the set of views that contribute to a given image. Selected rows or views in the selected angular range of super-views are weighted to generate synthesized views of the object in the plane of reconstruction. The synthesized views are weighted with scan weights, and then backprojected to produce a reconstructed image of the desired region of the object.

In one embodiment, helical weights over the range of super-views are determined. For example, the helical weights for a given row and a given source position are calculated by a function call such as:

$$\text{weight}=\text{hw\_func}(\text{zrow}-\text{zimage},\text{func\_type},\text{hw\_mode})$$

where zrow is a z coordinate of a row of detector 18 of CT imaging system 10, zimage is a z coordinate of the POR, func_type is an index into a generalized distance function; and hw_mode indicates whether interpolation or extrapolation is used. The helical weights are normalized so that the total for all rows contributing to a given image plane is a fixed value, for example, 1.0.

In one embodiment, z-smoothing is applied, and a loop over the number of images summed (i.e., number of z-smoothing kernel points) is performed to calculate the final scan weights. (This step is not performed in every embodiment.)

A subset of the superviews is weighted using the normalized helical weights (or the normalized helical and scan weights) and backprojected to produce the reconstructed image plane.

In one embodiment of the present invention, at least one high speed (HS) mode, high quality (HQ) mode and fast high quality mode (HQ-F) are provided. (Not all of these modes or types of modes are provided in every embodiment.) A minimum amount of data is acquired for at least one sampling of every line integral in an HS mode. At least two samples of every line integral are acquired in an HQ mode. Accordingly, in an HS mode, a half scan of super-views is acquired, while in an HQ mode, at least one or more rotation of views is acquired. For an HS mode and a fast high quality (HQ-F) mode, helical interpolation proceeds on a view-per-view basis, that is, without direct consideration of the conjugate rays (when such rays are available). Accordingly, helical interpolation/extrapolation proceeds on a row-to-row basis. (Helical interpolation takes place between two views acquired at the same source position, rather than between two conjugate measurements.)

Helical weighting is performed according to a general distance function calculation, such as a simple linear interpolation/extrapolation. However, a generalized distance function approach that smoothes the transitions from row-to-row is used to eliminate weight derivative discontinuities that occur with linear interpolation/extrapolation.

Higher order calculations from the 4 or 8 available samples available at each projection are performed to eliminate the weight derivative discontinuities that occur with linear interpolation/extrapolation. These higher-order calculations are performed without non-linear calculations on the data samples themselves to avoid changes in data flow that would otherwise make implementation more difficult. For example, the weight function w(z) may be non-linear as a function of z, but the data samples are combined linearly, e.g., $w(z-z_1)p_1+w(z-z_2)p_2$, where $p_1$ and $p_2$ are data. Weights are derived from a modified general interpolation function, for example, an apodized version of a sinc( ) function as used in Shannon-Whitaker interpolation.

In one embodiment, when using only two points for interpolation/extrapolation, a specific generalized distance function is used for which the sum of the weights for samples at the two points is 1.0, and for which the weight function does not have derivative discontinuities. When more than two points are used for interpolation/extrapolation, the weight sum is normalized to 1.0 without explicitly taking this constraint into consideration in the generalized weight function. Weights associated with each row contributing to a given estimate are calculated and then normalized by dividing each weight contribution by a sum of the weights. This normalization is independent of γ and therefore is done on the fly in one embodiment, because the interpolation is row-by-row.

Row-to-row interpolation, for each source position in the range of source positions considered, provides synthesized (estimated) projection data in the plane of reconstruction. Reconstruction then proceeds by applying a standard reconstruction technique developed for axial data sets. For example, in an HS mode of one embodiment, only a halfscan worth of projection data is synthesized in the reconstruction plane. Therefore, halfscan weights are applied to the projection data set, or more precisely, the weights applied to the projection data are normalized weights derived from the halfscan weights. The halfscan weights for part of the acquired projection data acquired with a source angle in $[0,2\pi]$ and centered on $\pi$ are written as:

$$\begin{cases} W_{HS}(\beta,\gamma) = \dfrac{\beta - \dfrac{\pi}{w} + \Gamma}{2(\Gamma-\gamma)} & \beta_{inf} = \dfrac{\pi}{2} - \Gamma \le \beta \le \beta^- = \dfrac{\pi}{2} + \Gamma - 2\gamma \\ W_{HS}(\beta,\gamma) = 1.0 & \beta^- \le \beta \le \beta^+ = \dfrac{3\pi}{2} - \Gamma - 2\gamma \\ W_{HS}(\beta,\gamma) = \dfrac{\dfrac{3\pi}{2} + \Gamma - \beta}{2(\Gamma+\gamma)} & \beta^+ \le \beta \le \beta_{sup} = \dfrac{3\pi}{2} + \Gamma \end{cases}$$

where $\Gamma$ is a maximum fan-angle.

A weight-smoothing transformation written as $f(x)=3x^2-2x^3$ is also applied, with $x=W_{HS}(\beta,\gamma)$.

Alternatively, parallel half-scan weights $W_{PHS}$ are derived from a parallel-beam formulation written as:

$$W_{PHS}(\beta,\gamma) = 1.0; \quad \dfrac{\pi}{2} - \gamma \le \beta \le \dfrac{3\pi}{2} - \gamma.$$

In multislice scanning, the cone-beam nature of the data acquired sometimes results in two measurements of the same ray in the POR being along rays at different angles through the patient with respect to the POR. Therefore, the halfscan weights also allow "blending in" the projection data inconsistencies that arise from the various cone-angles.

In one embodiment, overscan weights are used to handle data discontinuities that occur at the 0,2π interface even in the absence of patient motion. Extrapolation of projection data in z over half the extent of a macro-row is used. For example, extrapolation of projection data is performed so that a range of up to $(8/7)\times 2\pi$ worth of super-views contribute to a given image plane reconstruction. Because more than 360 degrees are available, overscan weights are applied to advantageously blend in cone-angle discontinuities that occur at the 0,2π interface. (More precisely, normalized overscan weights derived from overscan weights are applied.)

In one embodiment, the overscan weights used are those written as $f(x)=3x^2-2x^3$, where x varies between 0 and 1 in a view angle interval being considered. In another embodiment, the overscan weights used are those written as:

$$f(x) = \dfrac{\left|\sin(\dfrac{\pi}{2}(1+x))\right|^\delta}{\left|\cos[\dfrac{\pi}{2}(1+x)]\right|^\delta + \left|\sin[\dfrac{\pi}{2}(1+x)]\right|^\delta},$$

where x varies between 0 and 1 in an interval considered, and $\delta$ is a parameter.

In another embodiment, data acquisition is limited to exactly 360 degrees. In this embodiment, extrapolation is avoided by using underscan weighting, or more precisely, normalized weights derived from underscan weighting, to reduce artifacts that may arise from data inconsistencies. For example, a set of underscan weights already known in the art in an interval $[0,2\pi]$ are used in conjunction with an embodiment of the present invention. This set of weights is written as:

$$\begin{cases} W_{US}(\beta,\gamma) = 3x^2 - 2x^3 & 0 \le \beta \le \beta_U; & x = \dfrac{\beta}{\beta_U} \\ W_{US}(\beta,\gamma) = 1.0 & \beta_U \le \beta \le \pi - \beta_U - 2\gamma \\ W_{US}(\beta,\gamma) = 2 - (3x^2 - 2x^3) & \pi - \beta_U - 2\gamma \le \beta \le \pi + \beta_U - 2\gamma; & x = \dfrac{|\beta - \pi + 2\gamma|}{\beta_U} \\ W_{US}(\beta,\gamma) = 1.0 & \pi + \beta_U - 2\gamma \le \beta \le 2\pi - \beta_U \\ W_{US}(\beta,\gamma) = (3x^2 - 2x^3) & 2\pi - \beta_U \le \beta \le 2\pi; & x = \dfrac{(2\pi - \beta_U)}{\beta_U} \end{cases}$$

In one embodiment, variable reconstructed image thickness is provided by slice broadening using a z-smoothing approach, resulting in reduced helical artifacts and x-ray tube current. In discrete form, and in one embodiment, weights $W_{ZS}(\beta,\gamma)$ from a known z-smoothing approach are used in conjunction with one embodiment of the present invention. These weights are written as:

$$W_{ZS}(\beta,\gamma) = \sum_{i=1}^{T} h(i) \times W(\beta - i \times \Delta\beta, \gamma)$$

where:

h represents a z-smoothing kernel (such as {1/3, 1/3, 1/3});

T is the number of terms in the z-smoothing kernel (3 in the previous example);

$\Delta\beta$ is a view increment between each image plane contributing through z-smoothing to a final reconstructed image, and W( ) is an unsmoothed weight.

The most straightforward helical weighting functions are derived from linear interpolation/extrapolation expressions, however, it is known in the art that a linear model introduces discontinuities in the first derivative of the weights, which lead to a risk of streak artifacts when the POR crosses from one row into the next one. It is known that these risks are reduced by z-smoothing, and are further alleviated by using helical weighting functions such as an apodized sinc( ) weight function having a negative lobe feathered to zero. In general, $\Delta z_1 \neq \Delta z_2$, where $\Delta z$'s represent intervals between samples. These known smoothing techniques and weighting functions can be used in conjunction with embodiments of the present invention.

In another embodiment, a known SHE1 helical weighting is used for the helical weighting. The SHE1 helical weighting is written as:

$$hw(x) = \frac{NN}{DD};$$

where:

$$NN = \left|\sin\left(\pi\frac{1-x}{2}\right)\right|^\delta;$$

$$DD = NN + \left|\cos\left(\pi\frac{1-x}{2}\right)\right|^\delta; \text{ and}$$

$0 < x < 1.0$.

In another embodiment, known SHE2 helical weightings are used.

These weightings are written:

$$hw(x) = \sin^2\left(\pi\frac{1-x}{2}\right)$$

where $0 < x < 1.0$.

Embodiments of the present invention described are subject to a tradeoff when compared to known fast HS (HS-F) and HS algorithms. By using a significantly reduced number of views, embodiments of the present invention speed up processing and improve temporal resolution. In a few situations in some embodiments, a limited amount of extrapolation is used. On the other hand, presently known algorithms always interpolate between rays, but must fetch conjugate rays that are further apart in source angle and accordingly further apart in z, particularly for large fan-angles. Therefore, the known algorithms exhibit degradation in slice sensitivity profiles that are reduced when embodiments of the present invention are employed.

CT system 10 described herein is a "third generation" system in which both the x-ray source and detector rotate with the gantry. Many other CT systems including "fourth generation" systems wherein the detector is a full-ring stationary detector and only the x-ray source rotates with the gantry, may be used if individual detector elements are corrected to provide substantially uniform responses to a given x-ray beam.

From the preceding description of various embodiments of the present invention, it is evident that these embodiments advantageously provide weightings that depend upon not more than a distance between a detector row for a given source 14 position and the POR, whether interpolation or extrapolation is used, which generalized weight function is to be applied, and which mode of operation of CT imaging system 10 was used to collect the data. The helical weights thus depend only upon a source angle and not on a fan angle. Furthermore, through the use of interpolation or extrapolation, a much reduced number of super-views is used, resulting in reduced CPU processing time and improved temporal resolution. Residual data inconsistencies are handled through the use of HS weights in HS modes, and overscan or underscan weights in HQ-F mode.

While the invention has been described in terms of various specific embodiments, those skilled in the art will recognize that the invention can be practiced with modification within the spirit and scope of the claims.

What is claimed is:

1. A method for reconstructing a computed tomographic image of an object comprising the steps of:
   selecting an operating mode of a CT imaging system;
   helically scanning an object with a multislice CT imaging system in accordance with the selected operating mode to collect projection data;
   identifying a center view of the collected projection data for an image plane to be reconstructed;
   using the identified center view to select an angular range of super-views of the collected projection data that contribute to a reconstriction of an image of a desired region of the object;
   weighting selected rows or views in the selected angular range of super-views using helical weights to generate synthesized views of the object in the plane of reconstriction;
   weighting the synthesized views with scan weights; and
   backprojecting the weighted synthesized views to produce a reconstructed image of the desired region of the object.

2. A method in accordance with claim 1 wherein the helical weights are normalized to sum to a fixed sum, and the normalized helical weights are a function of not more than:
   a distance between a row of a scanner for a given source position and a plane of reconstriction,
   whether interpolation or extrapolation is used,
   which generalized weight function is applied for the weighting, and
   which mode of operation of the CT imaging system was used to collect the projection data.

3. A method in accordance with claim 1 further comprising the step of helically interpolating or extrapolating views of the collected projection data depending upon the selected operating mode of the CT imaging system.

4. A method in accordance with claim 3 wherein the interpolation or extrapolation is performed between more than two points.

5. A method in accordance with claim 1 further comprising the steps of applying a z-smoothing utilizing a z-smoothing kernel having a number of z-smoothing kernel points, and looping over a number of images summed corresponding to the number of z-smoothing kernel points to calculate the helical weights.

6. A method in accordance with claim 1 wherein the scan weights are derived from halfscan weights.

7. A method in accordance with claim 6 further comprising the step of applying a weight-smoothing transformation written as $f(x)=3x^2-2x^3$ with $x=W_{HS}(\beta,\gamma)$.

8. A method in accordance with claim 1 wherein the scan weights are derived from overscan weights.

9. A method in accordance with claim 8 wherein the overscan weights are those written as $f(x)=3x^2-2x^3$, where x varies between 0 and 1 in an interval of view angles considered.

10. A method in accordance with claim 8 wherein the overscan weights are those written as:

$$f(x) = \frac{\left|\sin\left(\frac{\pi}{2}(1+x)\right)\right|^\delta}{\left|\cos\left[\frac{\pi}{2}(1+x)\right]\right|^\delta + \left|\sin\left[\frac{\pi}{2}(1+x)\right]\right|^\delta},$$

where x varies between 0 and 1 in an interval considered, and $\delta$ is a parameter.

11. A method in accordance with claim 1 wherein the scan weights are derived from underscan weights.

12. A multislice CT imaging system for reconstructing a computed tomographic image of an object, said system configured to:

helically scan an object in accordance with a selected operating mode to collect projection data;

identify a center view of the collected projection data for an image plane to be reconstructed;

use the identified center view to select an angular range of super-views of the collected projection data that contribute to a reconstruction of an image of a desired region of the object;

weight selected rows or views in the selected angular range of super-views using helical weights to generate synthesized views of the object in the plane of reconstruction;

weight the synthesized views with scan weights; and backproject the weighted synthesized views to produce a reconstructed image of the desired region of the object.

13. A system in accordance with claim 12 configured to normalize the helical weights to sum to a fixed sum, and wherein the normalized helical weights are a function of not more than:

a distance between a row of a scanner for a given source position and a plane of reconstruction, whether interpolation or extrapolation is used, which generalized weight function is applied for the weighting, and which mode of operation of the CT imaging system was used to collect the projection data.

14. A system in accordance with claim 12 further configured to helically interpolate or extrapolate views of the collected projection data depending upon the selected operating mode of the CT imaging system.

15. A system in accordance with claim 14 configured to perform interpolation or extrapolation between more than two points.

16. A system in accordance with claim 12 further configured to apply a z-smoothing utilizing a z-smoothing kernel having a number of z-smoothing kernel points, and to loop over a number of images summed corresponding to the number of z-smoothing kernel points to calculate the helical weights.

17. A system in accordance with claim 12 wherein the scan weights are derived from halfscan weights.

18. A system in accordance with claim 17 further configured to apply a weight-smoothing transformation written as $f(x)=3x^2-2x^3$ with $x=W_{HS}(\beta,\gamma)$.

19. A system in accordance with claim 12 wherein the scan weights are derived from overscan weights.

20. A system in accordance with claim 19 wherein the overscan weights are those written as $f(x)=3x^2-2x^3$, where x varies between 0 and 1 in an interval of view angles considered.

21. A system in accordance with claim 19 wherein the overscan weights are those written as:

$$f(x) = \frac{\left|\sin\left(\frac{\pi}{2}(1+x)\right)\right|^\delta}{\left|\cos\left[\frac{\pi}{2}(1+x)\right]\right|^\delta + \left|\sin\left[\frac{\pi}{2}(1+x)\right]\right|^\delta},$$

where x varies between 0 and 1 in an interval considered, and $\delta$ is a parameter.

22. A system in accordance with claim 12 wherein the scan weights are derived from underscan weights.

\* \* \* \* \*

UNITED STATES PATENT AND TRADEMARK OFFICE
CERTIFICATE OF CORRECTION

PATENT NO.    : 6,341,154 B1
DATED         : January 22, 2002
INVENTOR(S)   : Besson It is certified that error appears in the above-identified patent and that said Letters Patent is hereby corrected as shown below:

Title page,
Item [*] Notice, delete the phrase "by 0 days" and insert -- by 2 days --

Signed and Sealed this

Nineteenth Day of October, 2004

JON W. DUDAS
*Director of the United States Patent and Trademark Office*

UNITED STATES PATENT AND TRADEMARK OFFICE
CERTIFICATE OF CORRECTION

PATENT NO. : 6,341,154 B1
DATED : January 22, 2002
INVENTOR(S) : Guy M. Besson

It is certified that error appears in the above-identified patent and that said Letters Patent is hereby corrected as shown below:

<u>Column 8,</u>
Line 9, delete "reconstricted" insert therefor -- reconstructed --.
Lines 12, 17 and 27, delete "reconstriction" insert therefor -- recontruction --

Signed and Sealed this

Fifteenth Day of March, 2005

JON W. DUDAS
*Director of the United States Patent and Trademark Office*